US009817949B2

(12) United States Patent
Poulin et al.

(10) Patent No.: US 9,817,949 B2
(45) Date of Patent: Nov. 14, 2017

(54) TEXT BASED PREDICTION OF PSYCHOLOGICAL COHORTS

(71) Applicant: Christian D. Poulin, Portsmouth, NH (US)

(72) Inventors: Christian D. Poulin, Portsmouth, NH (US); Paul Thompson, Hanover, NH (US); Linas Vepstas, Austin, TX (US)

(73) Assignee: Christian Poulin, Dover, NH (US)

( * ) Notice: Subject to any disclaimer, the term of this patent is extended or adjusted under 35 U.S.C. 154(b) by 184 days.

(21) Appl. No.: 13/803,120

(22) Filed: Mar. 14, 2013

(65) Prior Publication Data

US 2014/0222719 A1 Aug. 7, 2014

Related U.S. Application Data

(60) Provisional application No. 61/761,886, filed on Feb. 7, 2013.

(51) Int. Cl.
G06F 19/00 (2011.01)
G06N 5/04 (2006.01)

(52) U.S. Cl.
CPC .............. *G06F 19/345* (2013.01); *G06N 5/04* (2013.01)

(58) Field of Classification Search
None
See application file for complete search history.

(56) References Cited

U.S. PATENT DOCUMENTS

| 8,930,178 | B2 * | 1/2015 | Pestian et al. .................... 704/9 |
|---|---|---|---|
| 2003/0158467 | A1 | 8/2003 | Liebert |
| 2003/0180698 | A1 | 9/2003 | Salerian |
| 2005/0071198 | A1 | 3/2005 | Krupa |
| 2006/0122472 | A1 | 6/2006 | Pullman |
| 2006/0150989 | A1 | 7/2006 | Migaly |
| 2007/0112585 | A1 | 5/2007 | Breiter et al. |
| 2009/0240522 | A1 | 9/2009 | Handal |
| 2010/0088262 | A1 * | 4/2010 | Visel et al. .................... 706/18 |
| 2011/0118555 | A1 | 5/2011 | Dhumne et al. |
| 2015/0033120 | A1 * | 1/2015 | Cooke et al. ................. 715/271 |

OTHER PUBLICATIONS

Gotz, David, et al, "Visual Cluster Analysis in Support of Clinical Decision Intelligence," AMIA Annual Symposium Proceedings, 2011 pp. 481-490.*
Cover Sheet indicating date for Gotz, David, et al, "Visual Cluster Analysis in Support of Clinical Decision Intelligence," AMIA Annual Symposium Proceedings, 2011 pp. 481-490.*

* cited by examiner

*Primary Examiner* — Alan Chen
(74) *Attorney, Agent, or Firm* — Fish & Richardson P.C.

(57) ABSTRACT

Computer implemented techniques for classifying mental states of individuals are described. The techniques determine sets of words that are associated with multiple groups having different mental status, and a classification model is used to classify one group against another group. Furthermore, by determining points of intersection of words between a first group and second group, words that are statistically predictive terms and that are unique to each group, to provide further predictive features for differentiating the multiple cohorts.

20 Claims, 9 Drawing Sheets

FIG. 5

TEXT BASED PREDICTION OF PSYCHOLOGICAL COHORTS

This application claims priority under 35 U.S.C. §119 to U.S. Provisional Patent Application Ser. No. 61/761,886, filed Feb. 7, 2013, and entitled "Text-Based Prediction of Psychological Cohorts", the entire contents of which are hereby incorporated by reference.

CONTRACTUAL ORIGIN

The United States Government has certain rights in this invention pursuant to a sub-contract under Contract No. N66001-11-C-4006, Modification P00001 between the Space and Naval Warfare Systems Command (SPAWAR Systems Center Pacific), part of the United States Department of the Defense (Navy).

BACKGROUND

This invention relates to data analysis software.

Data is available in many forms for many topics and from many sources. The Internet is one example of a data source. The Internet has become an important tool to conduct commerce and gather information. Other sources of data include notes taken on observations including observations of patients that are seeking mental health services. One particularly affected population of individuals, some of which seek mental health services are current or former members of armed services, i.e., military personal.

SUMMARY

Described are processes including methods, computer program products and apparatus to build a mental state classifier, such as a suicidality classifier, e.g., a suicide ideation classifier based on the text contained within a set of records, such as medical records made by observations or other sources of data on individuals that can be used to classify an individual into one of a number of groups and provide an aid for a clinician in determining the mental health status, e.g., the suicide risk of prospective patients.

According to an aspect, a computer implemented process includes determining by one or more computers one or more data sets of words associated with multiple groups having different mental states define multiple cohorts, executing by one or more computers a classification model of a first group to classify against a second group, with the first and second groups being of the multiple groups, determining by one or more computers points of intersection of words between the first group and the second group, and determining by one or more computers words that are unique to each group to provide isolated statistically predictive terms from the multiple groups for predictive features for corresponding ones of the multiple cohorts.

According to an additional aspect, a computer implemented process includes determining by one or more computers one or more data sets of words associated with multiple groups having different mental states, executing by one or more computers a classification model of a first group to classify against a second group, determining by one or more computers points of intersection of words between the first group and the second group, determining by one or more computers words that are unique to each group to provide isolated statistically predictive terms from multiple groups for predictive features for the group, and applying a workflow process to reduce complexity in classification of groups or sub groups enabling a visualization of mental state cohorts for classification of risk.

According to an additional aspect, a computer program product tangibly stored on a computer readable storage device, the computer program product for mental state classification includes instructions for causing a processor to determine one or more data sets of words associated with multiple groups having different mental states define multiple cohorts, execute a classification model of a first group to classify against a second group, with the first and second groups being of the multiple groups, determine points of intersection of words between the first group and the second group, and determine words that are unique to each group to provide isolated statistically predictive terms from the multiple groups for predictive features for corresponding ones of the multiple cohorts.

According to an additional aspect, apparatus includes a processor, a memory coupled to the processor, and a computer readable storage device storing a computer program the computer program product for mental state classification includes instructions for causing a processor to determine one or more data sets of words associated with multiple groups having different mental states define multiple cohorts, execute a classification model of a first group to classify against a second group, with the first and second groups being of the multiple groups, determine points of intersection of words between the first group and the second group, and determine words that are unique to each group to provide isolated statistically predictive terms from the multiple groups for predictive features for corresponding ones of the multiple cohorts.

The following are some of the features within the scope of the above aspects.

A prediction is of mental health status of the groups. The prediction is of suicidality risk. The prediction is suicidal ideation. A military veteran population dataset is applied for suicidality prediction. Contextualized word pairs are formed to improve predictive accuracy. Model process applies a machine learning system, including Bayesian algorithms to the dataset to predict mental state. The model process applies a machine learning system that includes genetic algorithms and genetic programming systems to predict mental state.

One or more of the following advantages may be provided by one or more of the above aspects.

Described are processes including methods, computer program products and apparatus to build a mental state classifier, such as a suicidality classifier, e.g., a suicide ideation classifier based on the text contained within a set of records, such as medical records. The classifier is an aid for a clinician in determining the suicide risk of prospective patients by providing an output suggesting the likelihood of suicidal ideation. The suicide ideation classifier is in one embodiment derived from medical records that are free-text notes entered into a patient's record by a clinician. Models can be optimized for the best recall or for the best accuracy: the distinction is subtle but important. Roughly speaking, recall measures how well the classifier is able to identify true-positives, possibly at the expense of a high false-positive rate. That is, one would rather miss-identify someone as possibly suicidal, rather than the other way around. By contrast, maximizing accuracy avoids miss-classification, which is not necessarily a good thing medically.

DESCRIPTION OF DRAWINGS

FIG. 5 is an exemplary, alternative word cloud presentation.

DESCRIPTION

Figure 1:
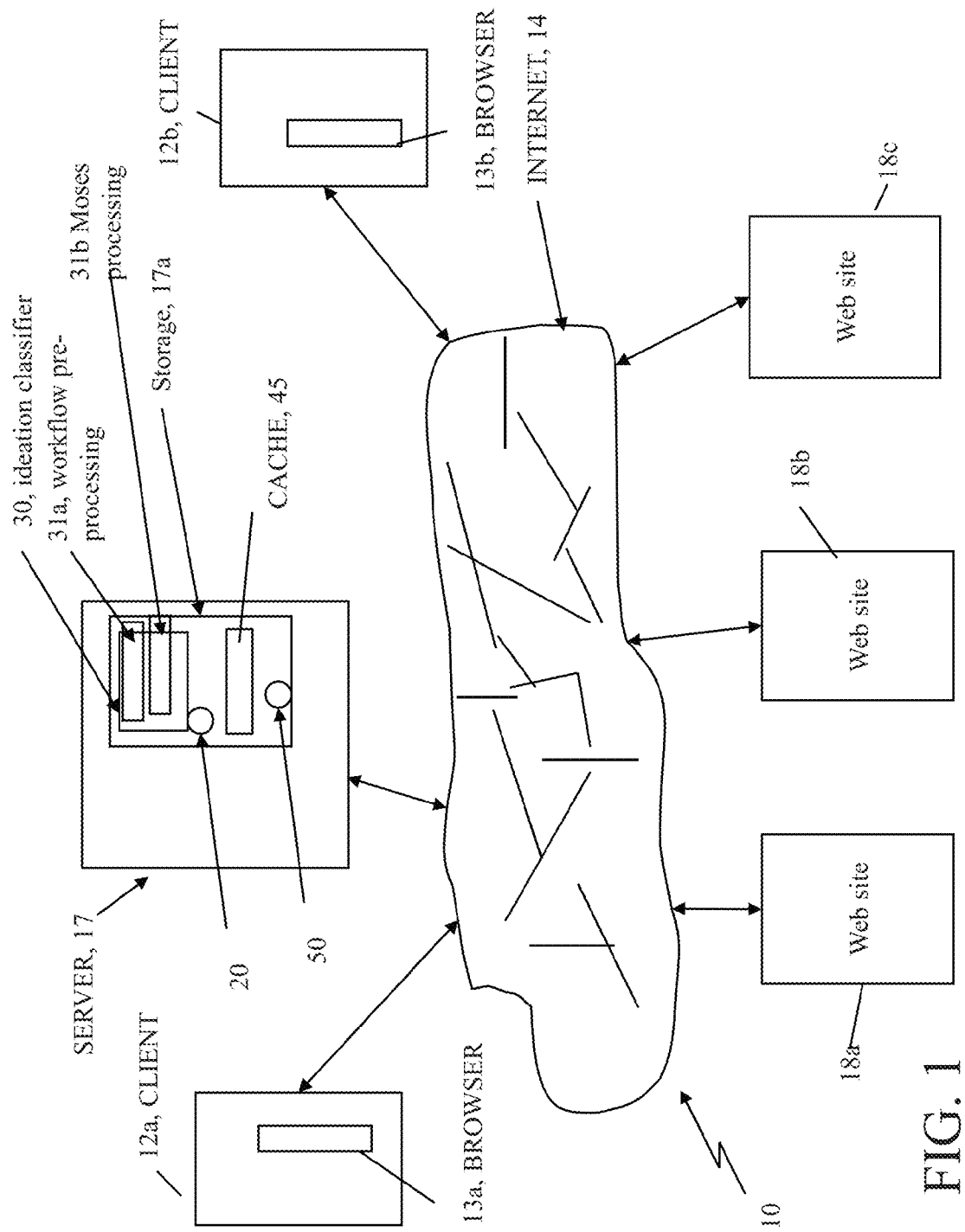
FIG. 1 is a block diagram of system employing data analysis software.

Referring to FIG. 1, a networked computer system 10 includes clients 12a-12b connected to a server system 17 through a first network, e.g., the Internet 14 or a private network. The clients 12a-12b run browser programs 13a-13b that can request the server computer 17 to invoke a mental state classification model such as an ideation classifier 30, as discussed below. The data analysis software 31a resides on a computer readable medium 17a, e.g., disk or in memory for execution. The data analysis software 31a analyzes data as discussed below. As one example, the data analysis software 31a analysis data obtained from, e.g., records of patients seeking medical attention, as will be discussed below.

Although the data analysis software 31a is shown in FIG. 1 residing on a server 17 that can be operated by an intermediary service, it could be implemented as a server process on a client system 12 or as a server process on a corporate or organization-based server. On the server 17 the data analysis software 31a includes analysis objects 20 that are persistent objects, i.e., stored on a computer hard drive 17a of the server in a database (not shown). At invocation of the data analysis software 31a, the analysis objects 20 are instantiated, i.e., initialized with parameters and placed into main memory (not shown) of the server 17, where they are executed through the data analysis software 31a.

As described below, the output from the data analysis software 31a is a result object 50 in the form of a prediction table that can be output as an HTML or equivalent web page. The result object 50 will include information as to a database or text representation of relationships between parent and child data. Formats for the data can be ".net" files (industry standard file format for a feature vector). Alternatively, other formats can be used such as a standard text file and so forth.

Figure 2A:
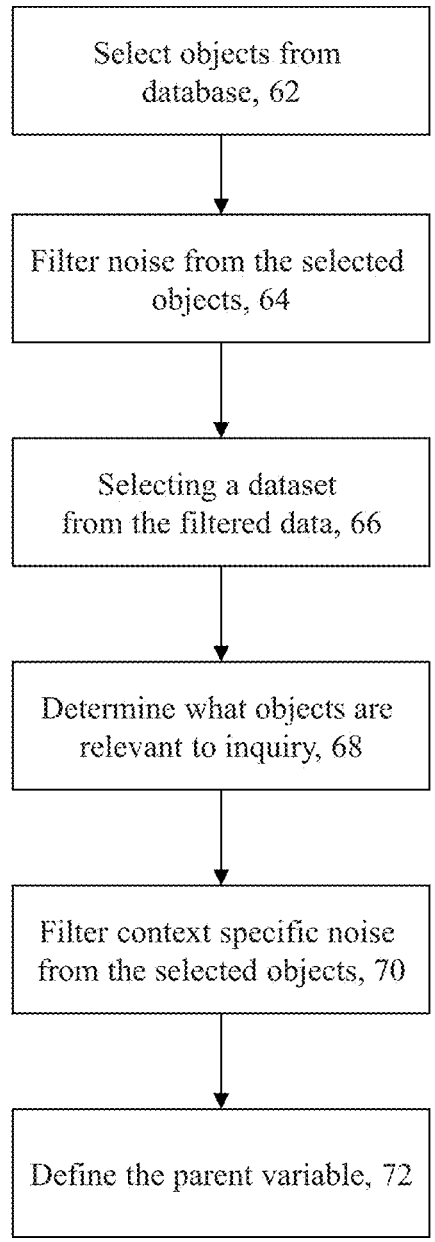
FIGS. 2A-2B are flow charts showing the data analysis software.
Figure 2B:
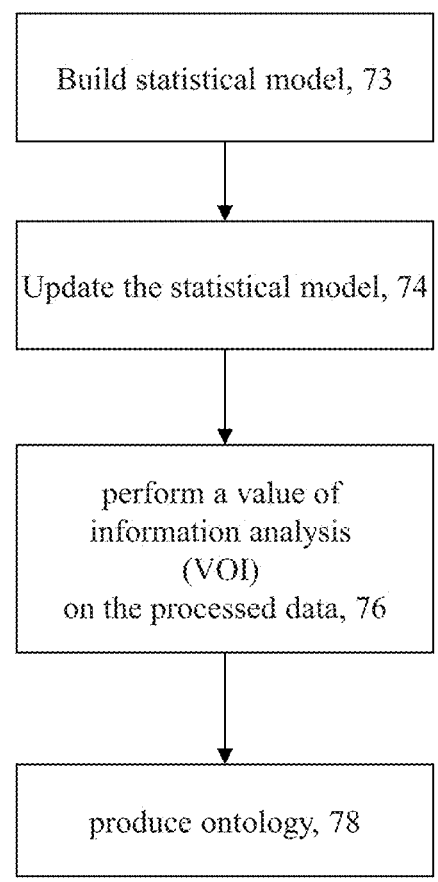

Referring to FIG. 2, the process of building an ontology based on data is shown. In the process 31a, preprocessing of the data is performed. A database containing text strings is selected 62. The text strings represent any alphanumeric text data and in particular represent records of patients seeking medical attention. The database of the text strings need not be in any particular structure. The process takes the text data from the database and filters 64 noise from the data. For example, if the data is initially retrieved in HTML format, the filtering process removes what would be considered noise in the process 31a such as HTML tags and scripts. There exist other types of noise at this stage for example, extra spaces, extra or inaccurate punctuation and irregular characters. In addition, noise can be somewhat problem specific, as is discussed below.

The data are selected 66 to provide a dataset that will be used to structure the data into child variables for analysis. The process 31a builds a parent and child relationship model from the dataset. The parent/child relationship model is defined as the parent variable being the desired outcome, e.g., how often would the process 31a expects to obtain a result, e.g., of parent possibilities. The child relationships are the prior knowledge that the process 31a examines to determine the parent possibilities. Given a known structure of text data, the state of probability is the prior knowledge, i.e., how many text data have been used out of that structure. The process 31a determines 68 what text data are relevant to the inquiry and the text data that needs to be examined by the process 31a. The process 31a chooses the actual variables to examine by choosing the child variables, e.g., the prior data for inclusion in a dataset.

Conditional probabilities are used to build the classifier's model and the eventual ontology. That is, relationships are determined for multiple child variables to the parent variable. Thus, while determining probabilities values uses conditional probabilities, basic probabilities (e.g., child to parent child to parent serial type of analysis) could also be used. Multiple routines determine conditional probability by measuring condition probability of each child variable based on the relevance of each child variable to the parent variable. The determined conditional probabilities are aggregated and compare aggregated conditional probabilities to parent.

A filter is employed 70 to remove context specific noise, e.g., data that are not relevant to the inquiry from the dataset. For example, time relevant data that is replaced by more time current data could be filtered out of the dataset, so that the data are not inadvertently included twice in the dataset.

The process defines 72 the parent variable. The parent variable can be an index, or particular variable inside the database. The parent variable is the variable that the process 31a is specifically trying to determine. A child variable can be chosen and promote to a parent variable.

The process builds 73 the statistical model from the dataset and parent variable. A statistical engine, algorithm or filter (hereinafter engine) defines the parent relationships between the child variables in the child variable dataset and the parent variable. The process determines incidence values for each of the child variables in the dataset. The incident values are concatenated to the data strings to provide the child variables. The child variables are stored in a child variable dataset.

One example of a statistical engine is a Bayesian Statistical engine to define correlative relationships. Others could be used such as a genetic algorithm as discussed below or other type of statistical classifier language. A statistical engine defines correlative relationships between child and parent variables. Other more complex relationships can be defined such as child to child relationships. The engine processes the dataset to produce child and parent variables that are defined by applying the engine to the dataset to establish relationships between the child and parent variables.

The Bayesian Statistical engine outputs node tables that represent the child and parent variables and their relationships, that is, the relationships are defined as the statistical relevance of one variable to other variables in the dataset. The parent and child nodes thus would include a value which represents the data <alpha numeric string> and statistical analysis relationships among other child and parent variable relationships. The process updates the statistical data in the node tables each time new data are included in the dataset because a static model might be predictive but, by updating the data used in the model on a dynamic basis, the updating may make the model more useful. The process need not define new relationships but merely places updated data in the proper defined relationships. A value of information analysis (VOI) processing estimates 76 how relevant a particular child is to the overall model. In addition, the VOI analysis can estimate how a change in one variable affects other variables. If a gap is detected in the data, the process estimates values for data using an extrapolation or other data estimation techniques.

The process defines 78 an ontology from the data using statistical techniques of correlation and inference and value of information analysis. The ontology is essentially a statistically collected group of node tables that represent a statistical correlation and relevance of the child variables to the parent variable.

Node tables depict the statistical relevance of discrete ranges for the parent variable being in a particular discrete range of each of the child variables, where the ranges of the parent and child variables correspond to a discretized, i.e., producing discrete divisions, of the ranges for the particular variable. That is, given the parent variable various ranges of the occurrence of particular words and corresponding ranges of the occurrences of parent variable will have different correlations to different ranges.

The ontology identifies which words are relevant based on how many times the words show up in the database. That is, the ontological representation is used to determine the structure of child variables as those child variables relate to the parent variable. A prediction for a value for the parent variable would be based on the ontological representation.

A prediction table can be rendered on a monitor or other output device is shown. The prediction table results from passing the node tables through the Bayesian engine. The prediction table displays prediction ranges for the variable.

Each dataset contains data relationships that are defined by rules that are yet to be discovered. The process that builds the ontology is used to find these rules, e.g., how the data objects in the collection of data in the database relate to each other.

A specific example of workflow preprocessing applying to finance is further set out in the issued U.S. Pat. No. 7,516,050 "Defining the Semantics of Data Through Observation," the contents of which are incorporated herein by reference.

Figure 3A:
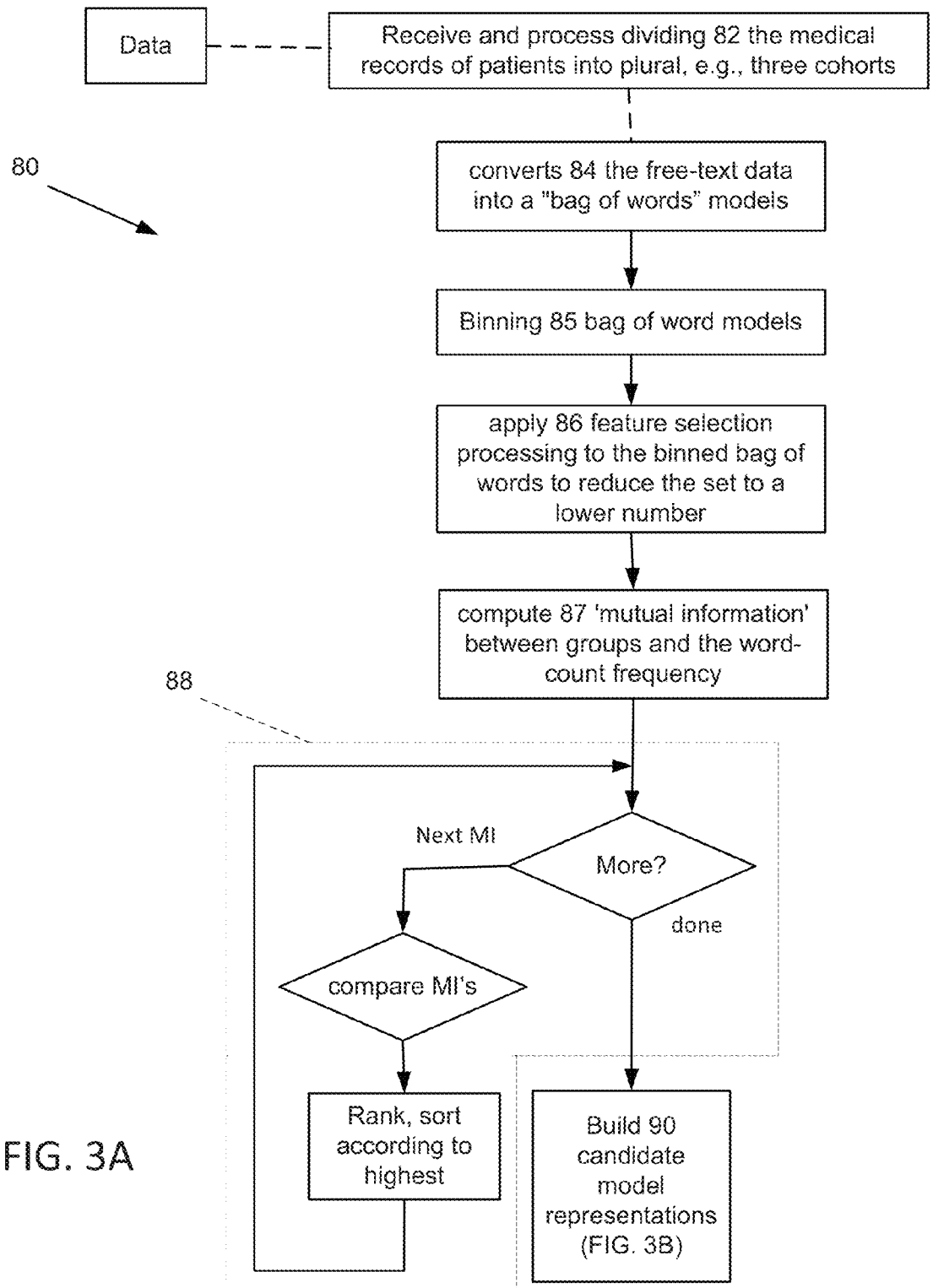
FIGS. 3A-3B are flow charts depicting a process for producing a mental state classification model.
Figure 3B:
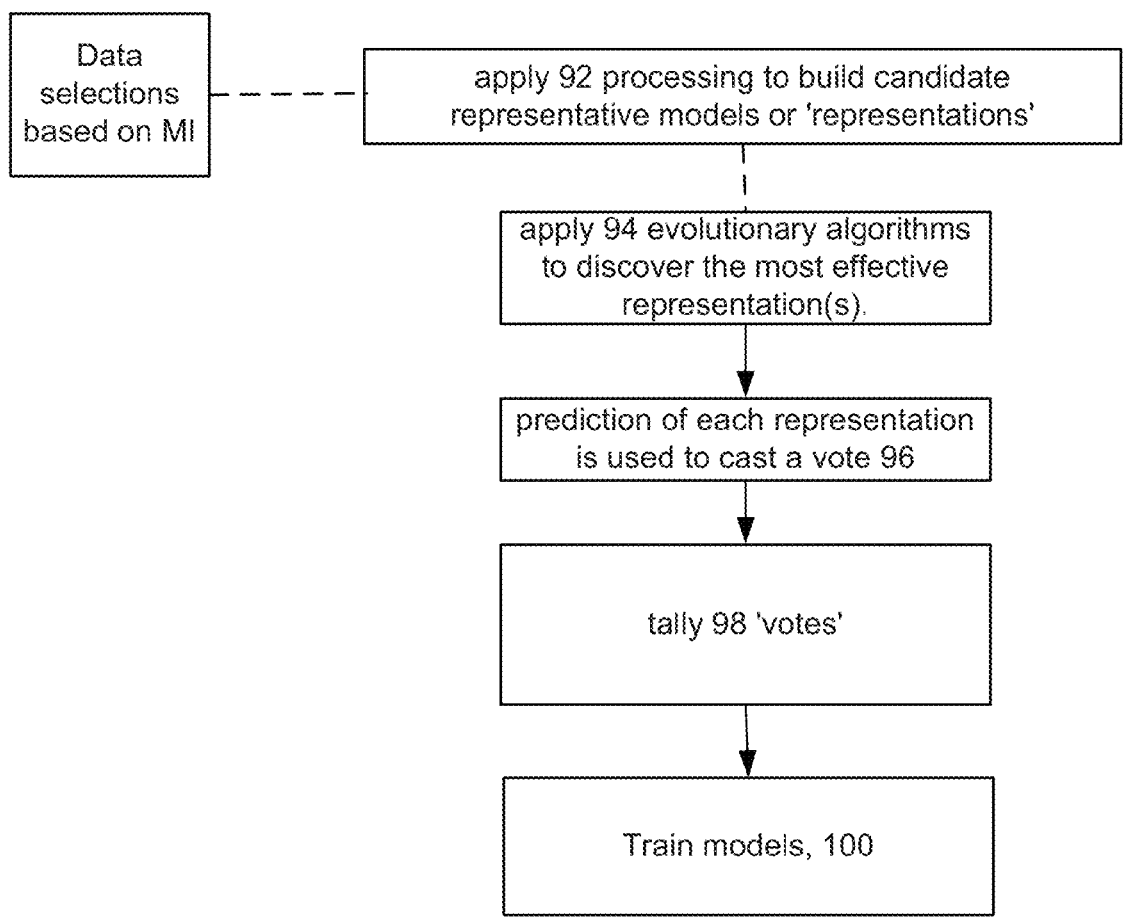

Referring now to FIGS. 3A-3B, a process 80 for producing a classifier 30 (FIG. 1) that classifies a first group of individuals against a second group of individuals, such as in mental state classification, e.g., "suicidality" classification and more specifically, a suicide ideation classifier 30 is shown. The suicide ideation classifier 30 is built based on the text contained within a set of records, such as medical records. The suicide ideation classifier 30 is an aid for a clinician in determining the suicide risk of prospective patients. The suicide ideation classifier 30 examines patient data, in this instance patient data recorded by a clinician, and assigns a risk level, green/yellow/red, suggesting the likelihood of suicidal ideation. The suicide ideation classifier 30 is built by using machine-learning techniques.

Model building process 80 builds the suicide ideation classifier 30 and includes dividing 82 the medical records of patients into three cohorts. The three initial cohorts are a control group of 100 patients (group 1), a suicide cohort of 100 patients (group 2), and a psychiatric cohort of 100 patients (group 3). The medical records are free-text notes entered into the patient's record typically by a clinician.

The model building process 80 converts 84 the free-text data into a "bag of words," i.e., a count of word frequency, e.g., a count of how often some given word are used in a particular patient's medical report for each patient in each cohort. Bag-of-words models completely ignore any sort of linguistic structure in the original text, as well as ignoring punctuation and any structural markup (paragraphs, sentence endings, etc.). Typically, 30 to 40 thousand different words are found, depending on which cohort is examined. Moreover, in some implementations "bag of phrases" models can be used. A bag of phrases model as with a bag-of-words model would ignore linguistic structure in the original text, as well as punctuation and structural markup (paragraphs, sentence endings, etc.), but would operate using concatenated words that form phrases.

Binning 85 is performed by producing bin-counts and lumping together similar words. The binning process helps to make up for relatively sparse data, by lumping together similar word-counts into the same category or 'bin'.

The model building process 80 applies 86 feature selection processing to the binned bag of words to reduce the set to a lower number. For example the set can be reduced by a factor of 2, a factor of 4 a factor of 10, e.g., in the example several thousand words according to how feature selection judges words being most significant in predicting outcome. The reduction may be done in several ways. One possible reduction removes words that occur less than a threshold, e.g., a few dozen times. Although the intent of this pass is to remove noise from the data, it is possible that perhaps some significant indicators are lost as well; thus data analysis includes experiments adjusting this reduction. Another possible reduction is to only count word stems: that is, to consolidate the counts for singular and plural forms of a noun, and to consolidate past, present and future tenses of verbs. The most important reduction is to choose only those words whose counts correlate well with the patient grouping. This is done by computing 87 the 'mutual information' (MI) between the group id (1, 2 or 3) and the word-count frequency.

The model building process 80, selects 88, the few thousand words with the highest MI to be used for model-building. Feature selection 88 has a counter-intuitive effect on the model: it is often the case that limiting the number of features used to build the model results in a better, more accurate model. This is because machine-learning algorithms can often focus in on irrelevant differences when classifying into groups: the differences are irrelevant, in that they fail to have predictive value. The greater the number of features (words) given to such a learning algorithm, the more likely it is to find such irrelevant differences; limiting the input to only the most significant features helps prevent such over-training. The model building process 80 builds 90 the model.

Referring now to FIG. 3B, building 90 the model includes applying 92 a workflow preprocessing and machine learning to build candidate representative models or 'representations' of the data selected based on the MI processing above, and applies 94 evolutionary algorithms to discover the most effective representation(s). An example of such a representation, one of many, trained on the current data, is shown in Table 1 below. The classifier 30 can include many representations, ranging from half a dozen to two or three dozen models. The prediction of each representation is used to cast a vote 96, e.g., in this instance make a prediction of risk level with an output 98 from the classifier 30 being a determination from a tally of the 'votes'.

To determine the accuracy and performance of the classifier 30, standard k-fold cross-validation techniques are used, with k=5. In this style of validation, the dataset is divided into 5 parts. Models are trained. Four of the parts are used to train a model, and the accuracy of the model is measured on the fifth part. This process is repeated each time leaving out a different fifth of the dataset, to be used for evaluation. The average of the five sessions may then be given as the overall accuracy.

Models can be optimized for the best recall or for the best accuracy: the distinction is subtle but important. Roughly speaking, recall measures how well the classifier is able to identify true-positives, possibly at the expense of a high false-positive rate. That is, one would rather miss-identify someone as possibly suicidal, rather than the other way around. By contrast, maximizing accuracy avoids miss-classification, which is not necessarily a good thing medically. To maximize the recall, while keeping the false-positive rate down to a reasonable level, training is done so as to maximize the F2-score, which is a certain reciprocal average of the recall and precision of the model.

TABLE 1

Example Representation or(and(or(and($MODERATE_t1.3 !$PRESCRIBE_t0.02) $CONCERN_t0.8 $EVIDENCE_t0.4 $INCREASING_t0.3 $RESTRICTED_t0.1) or($ALBUTEROL_t1.2 $AMOUNTS_t0.08 $SYSTEM_t0.08 $VIEW_t0.8) or(!$STOMACH_t0.4 !$SURROGATE_t0.7)) and(!$BRING_t0.6 !$HIGH_t1.9 !$MINUTES_t2.5 !$SAT_t0.7 $STOMACH_t0.4) $LOWEST_t0.08 $NYSTAGMUS_t0.03 $OLANZAPINE_t0.05 $OVERDOSE_t0.09 $PRESCRIBE_t0.02 $SUPERFICIAL_t0.16 $WEAPONS_t0.04 $WITHDRAWAL_t0.2)

The above is an example of a genetic algorithm representation, in this case, built from the dataset. The representation may be understood as follows: $MODERATE_t1.3 takes on a value of 'true' if the word 'moderate' occurs 1.3 or more times in the text (floating point values used in case word-counts have been normalized to non-integer values). The exclamation mark! indicates that the condition does not hold: so !$PRESCRIBE_t0.02 means that the word 'prescribe' does NOT occur 0.02 or more times. The Boolean operators 'and', 'or' serve to conjoin these conditions: thus the above is saying that, "if the word 'moderate' appears at least twice, and the word 'prescribe' does not appear, or if any of the words 'concern', 'evidence', 'increasing' or 'restricted' appear at least once, and the word 'albuterol' appears at least twice . . . then the patient should be classified as belonging to group 2."

Note that the original data set can contain many words, e.g., hundreds or thousands or more. In an example, approximately thirty-thousand unique words appear in the data. Out of the approximately thirty-thousand unique words the representation provides a small subset, illustrating the predictive power of a few terms in particular pattern of co-occurrence.

Dataset Statistics (A∪B) Example

Aspects of the Model building process 80 will be discussed in more detail below. Several versions of the data can be used, e.g., that occur at different times. One version, hereinafter referred to as the "Raw" version, is larger, but had data integrity issues. The second version, referred to as the "Clean" version, contains data on a subset of the patients in the Raw dataset. Specifically, the data is divided (82, FIG. 3a) into three sets of medical records:

Group 1: The control cohort. These are the records of 100 patients seeking medical attention, but not requiring any special psychiatric treatment. In the Raw set, there are 100, while in the Clean set there are 70.

Group 2: The suicide cohort. These are the records of 100 patients that committed suicide within a year of observation. In the Raw set, there are 69, while in the Clean set there are 69.

Group 3: The psychiatric control group. These are records of 100 patients requiring help with psychiatric issues; they had not committed suicide, but may be at risk. In the Raw set, there are 159, while in the Clean set there are 70.

The free text is converted (84, FIG. 3A) into bag-of-words by converting all punctuation into white-space, and using white-space as separators. The exceptions are word-phrases that included hyphens or underscores; these are simply removed to produce a single run-on word. Differences in capitalization are ignored by converting all words to uppercase. After this normalization, the Raw dataset is found to include over two million words; precisely, 2,158,421 words in this example. These are distributed across the three groups as follows:

Group 1: 246262 words, or 2462 words per patient.
Group 2: 398907 words, or 5781 words per patient
Group 3: 1513252 words, or 9517 words per patient The Clean dataset is statistically similar, but approximately half the size. This is primarily because the group with the greatest number of reports, group 3, is cut to less than half the size.

There are 32674 words in the Raw dataset that occurred at least once, but only 19124 that occurred twice or more. A rough sketch of the distribution is given in table 2. As can be seen, the active vocabulary of frequently used words is much smaller.

TABLE 2

Word Distribution

| Count | Number of occurrences |
|---|---|
| 32674 | once or more |
| 19124 | 2 times or more |
| 14975 | 3 or more |
| 12829 | 4 or more |
| 11497 | 5 or more |
| 8534 | 8 or more |
| 6111 | 16 or more |
| 4214 | 33 or more |
| 2824 | 66 or more |

Raw dataset word distribution.

The most frequently occurring words are shown in table 3.

TABLE 3

Most Frequent Words

| Word | $\log_2$ frequency |
|---|---|
| PERSON | −3.231 |
| THE | −4.678 |
| TO | −5.545 |
| AND | −5.785 |
| OF | −6.075 |
| PATIENT | −6.479 |
| FOR | −6.505 |
| HE | −6.676 |

The frequency of a word is obtained by taking the number of times the word occurs, and dividing by the total word count. The log 2 of the frequency denotes the logarithm base-2. Thus, "person" occurs approximately 23 thousand times, or 0.1=2-3.23 fraction of the time. Shown are frequencies for the Raw dataset.

Word-pairs are also explored, as these can have a predictive power as well. Word pairs are constructed by considering adjacent words, as well as pairs one word apart (ignoring the word in the middle). Thus, for example: "big red balloon" generates two word pairs: "big_balloon" and "red_balloon". The total pair count is thus twice the total word count. There are 791283 unique word pairs; of these, 63283 occurred 8 or more times, 32888 occurred 16 or more times, 16530 occurred 32 or more times, and 7716 occurred 64 or more times.

Not all word pairs are equally interesting. Semantically meaningful word pairs are those with high mutual information between them. Mutual information (MI) for a pair of words x,y is defined as;

$$MI(x, y) = \frac{p(x, y)}{-\log 2 p(x, *) p(*, y)}$$

Here, p(x,y) is the probability of seeing the word pair x,y, divided by the total number of word pairs. The two probabilities p(x,*) and p(*,y) are the probabilities of seeing any word pair, whose first word is x, or last word is y, respectively. MI scores typically range from slightly above 20 to less than zero. Examples of word pairs, from this dataset, with an MI of about 20, include ULTERIOR_MOTIVES, HLTHY_LVNG, VOCALIZES_INTELLIGIBELY, GIN_TONICS, ROAST_BEEF, MARATHON_RUNNER, GOVERNMENTAL_ENTITIES. By contrast, lower MI scores are less meaningful examples of MI of 4 include: HUNGRY_HAD, HAD_SWEAT, INTERACT_IN, RX_IBUPROFEN, ANYTHING_HIMSELF while those with an MI below zero degenerate into nonsense: MORPHINE_YOU, RECOVERY_ARE, HIS_HOW, YES_WITH. A later section de-scribes an attempt to produce a model using a dataset that included all word pairs with an MI greater than 4, and occurred at least 16 times in the text.

Binning

Prior to performing training on the dataset, bin-counts are produced. The binning process (85, FIG. 3A) helps to make up for relatively sparse data, by lumping together similar word-counts into the same category or 'bin'. This serves to further simplify the data and boost the performance of the training step. Binning is performed by determining the probability distribution of a given word; that is, by determining the average number of times it occurs (across all patients), and the standard deviation about this average (as it varies from patient to patient). These two numbers provide a natural size that allows a word count to be assigned to a bin. For example, given an average, once might say that, for a given patient record, a given word occurs more than average, or less than average, thus yielding two bins total.

Another possibility is to use three bins: for a given patient, a word may occur about an average number of times (to within one standard deviation away from this average), or well-below average (more than one standard deviation below average), or well above average (more than one standard deviation above average). It will be seen, in a later section, that best results are obtained by using two to five bins.

The results of binning are Boolean-valued features. So, for example, if the term 'PTSD' occurs an average of 2 times per patient record, a two-bin system would provide one feature for this word: (PTSD>2) which is either true or false for a given patient record. If, for example, the standard deviation is 1.0 for this word, a three-bin system would include two features for this word, set at one standard deviation above and below average; that is, (PTSD>1) and (PTSD>3), each of which may be separately true or false for any given patient record.

Given 31 thousand distinct words, a two-bin system would produce 31 thousand features, while a three-bin system would result in twice as many: 62 thousand Boolean-valued features. A four-bin system would result in three times as many features, and so on.

Feature Selection

After binning, but before building a model, the dataset, now converted into a collection for true/false bin assignments, is run through a static feature-selection process (86, FIG. 3A). This is done to reduce the size of the dataset, from tens of thousands of features, less a fewer number, e.g., tens of features to hundreds to one to three thousand features. As noted previously, the dataset only contains about four thousand words that get used 33 or more times, so it seems reasonable that words which only occur in a few patient records are not going to serve as reasonable predictors of behavior. Given that there are about 330 patient records total, a word that occurs less than 33 times in the total dataset will occur in less than one in ten patient records anyway. The validity of using or discarding rare words will be discussed further in the data analysis section below.

Because the run-time speed of the next stage, model-building, is not strongly affected by the number of features that it is given, it is safer to err on the side of giving it too many features to choose from (thousands), rather than too few (hundreds) although in some instances fewer features could be used.

As a result, a very simple and efficient feature selection algorithm suffices (88, FIG. 3A). The algorithm used is to choose those features that have the highest mutual information with the desired patient classification. The mutual information is computed (87, FIG. 3A) as:

$$MI(x, y) = \frac{p(x, y)}{-\log 2 p(x, *) p(*, y)}$$

except that here, the variable x is taken as the classification of a patient belonging to one group or another, while the variable y is taken to denote whether a given feature is true or false. Thus, if a certain feature is true whenever the patient belongs to group A, we expect MI(A, true) to be large; likewise, it may anti-correlate: MI(A, false) may be large. To continue with the previous example, the mutual information MI("group1", (PTSD>2)) is computed for the word 'PTSD'. If this MI ranks (88, FIG. 3A) in the top few thousand, then (PTSD>2) is accepted as a valid feature, worth exploring during the training stage. Words that occur equally often in one group as another will have a low MI score, and thus will not be selected. The reason for choosing MI, as opposed to some other measure, is that it does not strongly discriminate against rare words. Thus, a word which occurs infrequently (say, in only one out of ten patient records), but still correlates very well with the patient grouping (occurring, for example, only in group 2 patients), such a word may still have a reasonable MI score, and thus will be eminently suitable for use in classifier 30.

Model Building (A|B)

Model building (90, FIG. 3A, 3B) is a CPU intensive stage of processing for the production of models of the data.

This sub system 31b implements a machine learning approach (92, FIG. 3B), e.g., by using a genetic programming classifier that searches through a very large set of representations, such as that shown in TABLE 1, and determines those representations that most accurately fit the training data.

One such genetic programming classifier (94, FIG. 3B) can be based on Meta-Optimizing Semantic Evolutionary Search (MOSES). The algorithm implemented by MOSES is discussed in several references See for example Moshe Looks. Competent Program Evolution, Doctor of Science, thesis Washington University, St. Louis, USA, 2006 incorporated herein by reference.

The sub system 31b starts by producing a program tree (in the current usage, a tree of Boolean operators, such as that shown in table 1). The nodes and leaves of the tree are free to vary over the full range of input variables, as well as to vary over the Boolean operators (and, or, not). For any fixed choice of nodes and leaves, the resulting tree may be scored against the input training data (the features) to see how well it fits; clearly some choices will be better than others. The set of all possible node and leaf settings are explored using a genetic evolutionary search algorithm combining hill-climbing and genetic cross-over. When no further improvements are found, the process is begun again, this time with a different, and usually, a more complex program tree. This step is again repeated until either a perfect score is reached, or set time-limits are exceeded.

The result of this process is a large number of representations, each of which model the training data more or less equally well (96, FIG. 3B). The ensemble of these representations is then referred to as the model (98, FIG. 3B). This model is effectively a distilled, compressed version of the training data.

The model classifies the training to see which patient belonged to which cohort. Given the form of the model, it may be used classify new patients; that is, to make predictions about the value of the dependent variable (the patient classification) based on new and different input variables (word counts). Classification is done by presenting the same inputs to each of the representations, with each representation making a prediction: a majority vote is then taken to determine the final classification (96, FIG. 3).

The theoretical validity of using the model for classification in this way is founded on the belief that the model captures something essential about the way that words are used in text. This is a reasonable belief, given industry experience with bag-of-words classifiers. The practical validity of the model can be tested in several ways; k-means cross-validation will be used here.

Cross-Validation

In order to test the validity of the models, k-means cross-validation is performed, with k=5. The input dataset is split into k subsets, with each subset containing 1/k of patient records. Training is then performed using k−1 of these subsets as input, and a model is built (that is, a model is built on ⅘'ths of the data). The accuracy of the model is then evaluated on the subset that is held out (on the remaining ⅕th). This process is repeated k times, to obtain k models, and k different accuracy test results. The test results are then averaged together to obtain an estimate to the overall system accuracy. That is, if a model is trained on the full data-set (without any hold-outs), the accuracy of this resulting model, on new, blind data, is expected to be similar to the cross-validated accuracy.

During cross-validation, four different statistics are gathered: the number of true-positives, false-positives, true-negatives and false-negatives. All models are built as binary classifiers, so that 'positive' refers to membership in cohort 2: the suicide positive cohort. Thus, in this case, false-positives are those who are incorrectly classified as suicidal, whereas false-negatives are patients whose suicide is not foreseen. In order to be a clinically useful system, it is probably best that, if the system erred, it did so by finding too many false positives, rather than by failing to detect a suicidal patient (a false negative). There are five different variables that capture this idea in different ways: the 'recall', 'precision', 'accuracy', F1-score and F2-score. The 'recall' addresses the question "are all true positives identified (at the risk of some false positives)?" The 'precision' is the opposite: "are false positives minimized (at the risk of failing to identify some true positives)?" Accuracy, F1 and F2 are different ways of blending these together to obtain reasonable composite scores. Presuming that the having a high recall is the clinically desirable way to classify patients; the F2-score is then probably the best quantity to maximize. Note that maximizing F2 can hurt accuracy (i.e. too many false positives), while maximizing accuracy can lead to more false-negatives than might be desirable.

Mathematically, these five quantities are defined as follows.

$$\text{recall} = \frac{TP}{TP + FN}$$

$$\text{precision} = \frac{TP}{TP + FP}$$

$$\text{accuracy} = \frac{TP + TN}{TP + FP + FN + TN}$$

$$F_1 = \frac{2 \times \text{precision} \times \text{recall}}{\text{precision} + \text{recall}}$$

$$F_2 = \frac{5 \times \text{precision} \times \text{recall}}{4 \times \text{precision} + \text{recall}}$$

Here, TP stands for 'true-positive', and so on. All five quantities can vary between 0 and 1. For a system with a perfect score, all five quantities would equal 1. If all classification is done by random chance, then all five quantities would equal 0.5. Thus, in general, it is desired that all five quantities should be above 0.5. Note that it is possible to have a classifier that scores above 0.5 for some of these measures, and below 0.5 for others.

Cross-validation runs are performed to train classifiers on both the initial Raw and final Clean data-sets, to distinguish group 1 (controls) from group 2, and to distinguish group 3 (psych patients) from group 2. Results are reported in a series of tables. Each table is of the form shown in table 4.

TABLE 4

Example Confusion Matrix

|  | Predicted negatives | Predicted positives |
| --- | --- | --- |
| Expected | Numb. of true negatives | Numb. of false |
| Expected | Numb. of false | Numb. of true |

Results are reported in the form of the above confusion matrix. Scores for this matrix are given by the equations (1).

Results: Group 1 Vs. Group 2

The Clean dataset contains 70 patients in group 1 (control group) and 69 patients in group 2. The resulting models, and their descriptive ability, depend somewhat on the training parameters, such as run-time, the number of features selected, and other variables. In all cases, the models fit the training data very well. One such case is shown in table 5. The results for the best-fit model on the test set are shown in table 6.

TABLE 5

Training Confusion Matrix, Group 1 vs. Group 2

|  | Predicted Grp 1 | Predicted Grp 2 |
|---|---|---|
| Expected Grp 1 | 277 | 3 |
| Expected Grp 2 | 11 | 265 |

Confusion matrix for the training set. The model predictions are shown in the columns, the expected results in rows. There are 4×(70+69)=556 training records to be classified in a 5-fold cross validation.

| Accuracy | 0.974 | (542 correct out of 556 total) |
|---|---|---|
| Precision | 0.988 | (265 correct out of 268 total) |
| Recall | 0.960 | (265 correct out of 276 total) |
| FP Rate | 0.010 | (3 false pos out of 280 total) |
| F_1 Score | 0.974 | |
| F_2 Score | 0.965 | |

| Accuracy | 0.582 | (81 correct out of 139 total) |
|---|---|---|
| Precision | 0.596 | (34 correct out of 57 total) |
| Recall | 0.492 | (34 correct out of 69 total) |
| FP Rate | 0.328 | (23 false pos out of 70 total) |
| F_1 Score | 0.539 | |
| F_2 Score | 0.510 | |

The results shown here are for a model trained on a set of 3000 pre-selected features, dynamically narrowed to 240 features during the run. Input features are produced by partitioning the word-counts into 3 levels, with thresholds placed one standard deviation above and below average. This model is selected to maximize accuracy, rather than recall or F2 score. Other models achieve superior recall rates and F2 scores, as can be seen in FIG. 2.

The following shows the list of words that appear a model distinguishing group 1 and group 2. It is trained using the same parameters as those reported in table 6. In tables 7 and 9 and results tables below, there are provided words, acronyms, and in some instances misspelled words. The misspelled words are intentional either being an existing artifact of clinician notes or how the clinician notes were inputted into the algorithm.

TABLE 7

Model Words, Group 1 vs. Group 2

ABSENCE ACCEPTED ACCIDENT ACCURACY ACTIVITY ACTUALLY ADDITION ADEQUATELY ADMITS ADR AFFECT AFRICAN AGAIN AGGRAVATED AGITATION AID ALLOW ALPHABETIZED ALREADY ALTERATION ALTERNATIVES AM ANALGESIA AND ANOREXIA APPROPRIATE ARTHRALGIA ARTHRITIS BLINDNESS BOTTOM BROCHURE BRUIT CALCULATION CAMERA CASUALLY CATEGORY CATHETERIZATION CCS CENTERS CITY CLARIFY CLOTHES COMP COMPENSATION COMPREHENSIVE CULTURAL CUTTING DECLINES DELUSIONAL DEMEROL DFE DIAGNOSTIC DLCO DOCUMENTS DOOR EARS EDUCATED EGGS ELSE ENDS ESCORT EXERCISE EXPERIENCING EXTREME FATAL FATIGUE FEEDS FILLED FINGERSTICK FLUVIRIN FOODS FORMAT GOT GRAM GUILLAINBARRE HABITUAL HALF HAPPENS HELPING HES HGBAC IMAGES INTEGRATED INTERMITTENT INTERPERSONAL ISSUE ITEMS LABORATORY LADDERS LAND LIFESUSTAINING LIPIDS LIVE LUMBAGO MEMORIAL MIW MODIFICATION MOVING MYALGIAS NECK NEUTRAL NOTHING NW ONCE OPTICAL OS OW PERFUSION PERIODICALLY PERTAINING PLASMA PLENTY PLS POH POINTS POLYPHAGIA POSTIVE POSTOP PRIVATE PROTECTOR PURPOSES PYLORI RART READ READY REASONS RECHECK RECIEVED REDUCING REQUESTING REQUESTS RESPONSIBILITIES RETROFLEX-ION RETURNED REVEALED RIDING RONCHI SCOOTER SCREENED SCREENING SECRETIONS SEEKING SEES SERVED SHAMPOO SOON SPECIALIST SPINAL STARTLED STENOSIS SUTURED SYST TAKES TECHNIQUES TELCARE TELL TENSE TERMINAL TETANUS THRU TN TRANSFERED TRIAGE TRIAL TRIED TRIGGERS TRIGLYCERIDE TRY TWISTING UARY UNSTEADY UROLOGIC VERBALIZED VERBALLY VERIFICATION VESSEL WALKIN WANTED WBC WENT WHILE WHO WHOLE WIFES WISH WISHES WORRIED YEARS YESTER

The results shown here indicate that the model that is produced fits the training data very well, excelling in all measures. This is to be expected for the training set.

TABLE 6

Test Confusion Matrix, Group 1 vs. Group 2

|  | Predicted | Predicted |
|---|---|---|
| Expected | 47 | 23 |
| Expected | 35 | 34 |

Confusion matrix for the test set. The model predictions are shown in the columns, the expected results in rows. There are 70+69=139 test records to be classified in a 5-fold cross validation.

Results: Group 3 Vs. Group 2

The Clean dataset contains 70 patients in group 3 (psych group); the classification goal is to treat these patients as negatives, despite the fact that they exhibit many of the same psychological issues the goal is to find differentiating factors. Results of 5-fold cross-validation are shown in table 8.

TABLE 8

Test Confusion Matrix, Group 3 vs. Group 2

|  | Predicted Grp | Predicted Grp |
|---|---|---|
| Expected Grp | 43 | 27 |
| Expected Grp | 22 | 47 |

Confusion matrix for the test set. The model predictions are shown in the columns, the expected results in rows. There are 70+69=139 test records to be classified in a 5-fold cross validation.

| | | |
|---|---|---|
| Accura | 0.6 | (90 correct out of 139 total) |
| Precisio | 0.6 | (47 correct out of 74 total) |
| Recall | 0.6 | (47 correct out of 69 total) |
| FP Rate | 0.3 | (27 false pos out of 70 total) |
| F_1 | 0.6 | |
| F_2 | 0.6 | |

The results shown here are for a model trained on a set of 3000 pre-selected features, dynamically narrowed to 500 features during the run. Input features are produced by partitioning the word-counts into 2 levels, with a threshold at the word-count average. This model is selected to maximize accuracy, rather than recall or F2 score; however, it appears to have the best F2 score of all those explored.

The following shows the list of words that appear a model distinguishing group 3 and group 2. It is trained using the same parameters as those reported in table 8 Note that this set of words is entirely different than those that distinguish groups 1 and 2. Note in particular the presence of emotion laden words.

TABLE 9

Model Words, Group 3 vs. Group 2

AA AAA ABOUT ADULT AFRAID AGGRAVATING ALIGNMENT ALOH ALOT ANAND ANT ANTIPSYCHOTIC APPOINT AROUSE BARS BLOCKERS BRONZE CAHNGE CANCERS INCLUDEANTLY CRYING DEMONSTRATING DENT DESPONDENT DIRECTORY DISHEVELED DISORDER DOCUSATE DPT DRUSEN EFFECTED EPIDERMAL FEAR FRIGHTENING GEROPSYCHIATRY HC ICDCM INTERMITTANT LIPITOR LUQ MEALTIME MGOH MONFRI NALCOHOL NEUT NOBODY NOCTURIA NOTABLY OBESITY OUTSTANDING PRACTICING PRE-FILLED PREOCCUPIED PRESBYOPIA PRIVATE PSYCHIATRICALLY PUNCTUM QUADRANTS RANGES REGAINED REORDER RESIDENTIAL RESTRICTED RUMINATES SHAVE SPARE SPECIMEN SPELL SPLITTING SSN STAIN STANDARDS STRAIGHTENED STRANGE STREET STRUGGLES STUDENT STVHCS STX STYLE STYLES SU SUBLUXATION SUBSALICYLATE SUPERVISOR SUPERVISORS SUPPLY SWABS SYMPTOMS TACH TE TEACHER TEASPOONFUL TEETH TELEMETRY TEMAZEPAM TEMPOPORMAND TFTS THI THY TIB TON TOP TOPICAL TP TRANSFUSIONS TRAVELS TRAZODONE TURMOIL TUSCON TWAVE UC UCINATIONS UES ULTIMATELY UNCHANGED UNCOOPERATIVE UNDERGONE UNHAPPY UNIQUE UNMARRIED UNPLEASANT UNRESECTABLE UNSP UNT UPCOMING URINATED USEFULNESS VALLEY VERIFIED VET VIDEOS VIRTUE VISA VISIT VISUALIZATION VIT VOIDING VOLUME VTACH WALKIN WARNING WARRANT WATCHES WELLGROOMED WHEN WHIP WILLING WORTHLESSNESS WOUNDED WTIH XPATIENT YE YEAR YOUNGER ZER

ROC Curves

The receiver operating curve (ROC) for several models trained to distinguish group 1 and 2 are shown. This curve is for the Clean dataset, of 70+69 patient records.

Figure 4A:
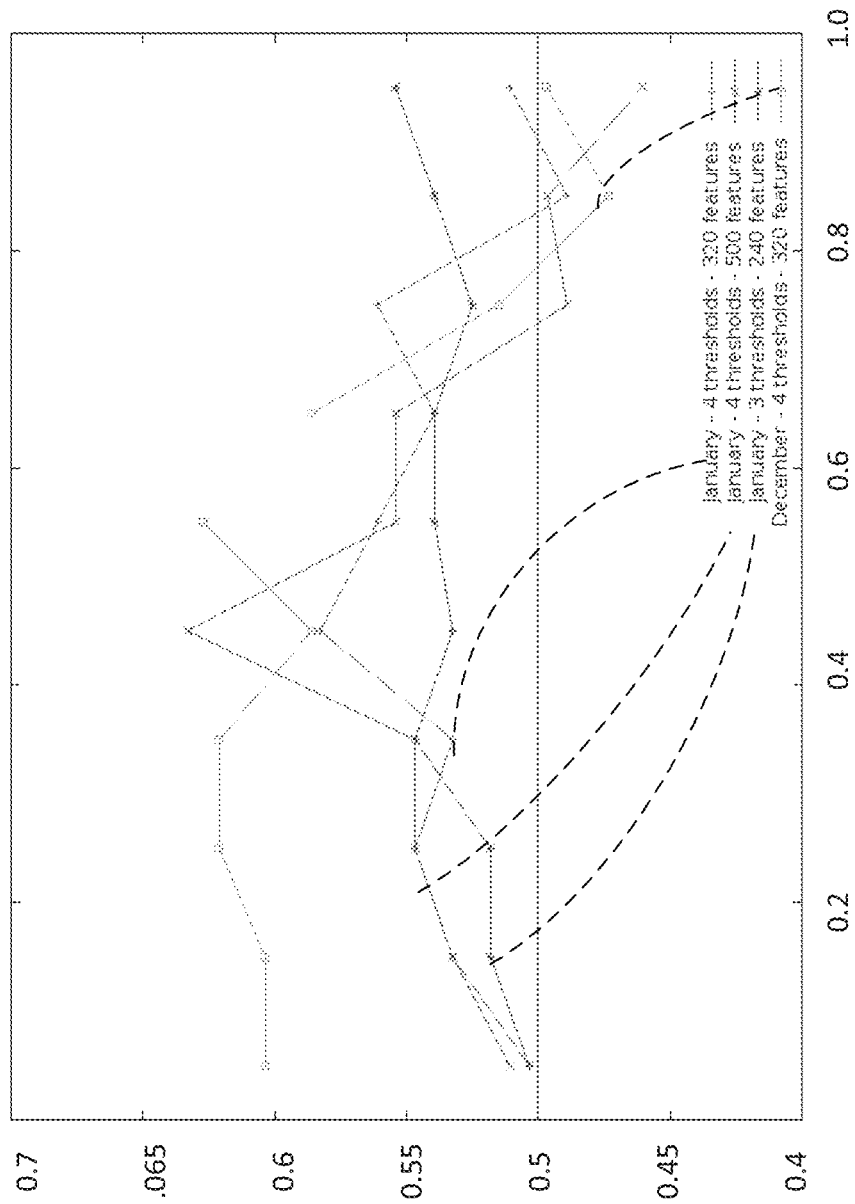
FIGS. 4A-4C are a series of graphs depicting statistical relationships.

Referring to FIG. 4A a graph plot of an ROC Curve of Group 1 vs. Group 2 is shown. This graph shows the "receiver operating curve" (ROC) obtained for three different sets of training parameters. Each data point is obtained via one run of 5-fold cross-validation, for a fixed set of parameters. Each collection of line segments is the result of training so as to maximize, while holding the nominal recall rate (y-axis) at or above a minimum required value. The un-referenced line along the horizontal indicates the expected score for models classifying purely by random chance. A single training run is shown. These runs also differ in the number of features that are dynamically selected during the run. The data shown is for the Clean dataset, including 70 patients in group 1 and 69 in group 2.

This graph shows the accuracy on the test set, as a function of the nominal training-set recall. The models are trained so as to maximize precision, while holding the recall above a minimum level: the "nominal training recall" is that minimum level. Also included in this figure are results on the Raw 2012 dataset, which while more accurate, is a less clean/reliable set.

Figure 4B:
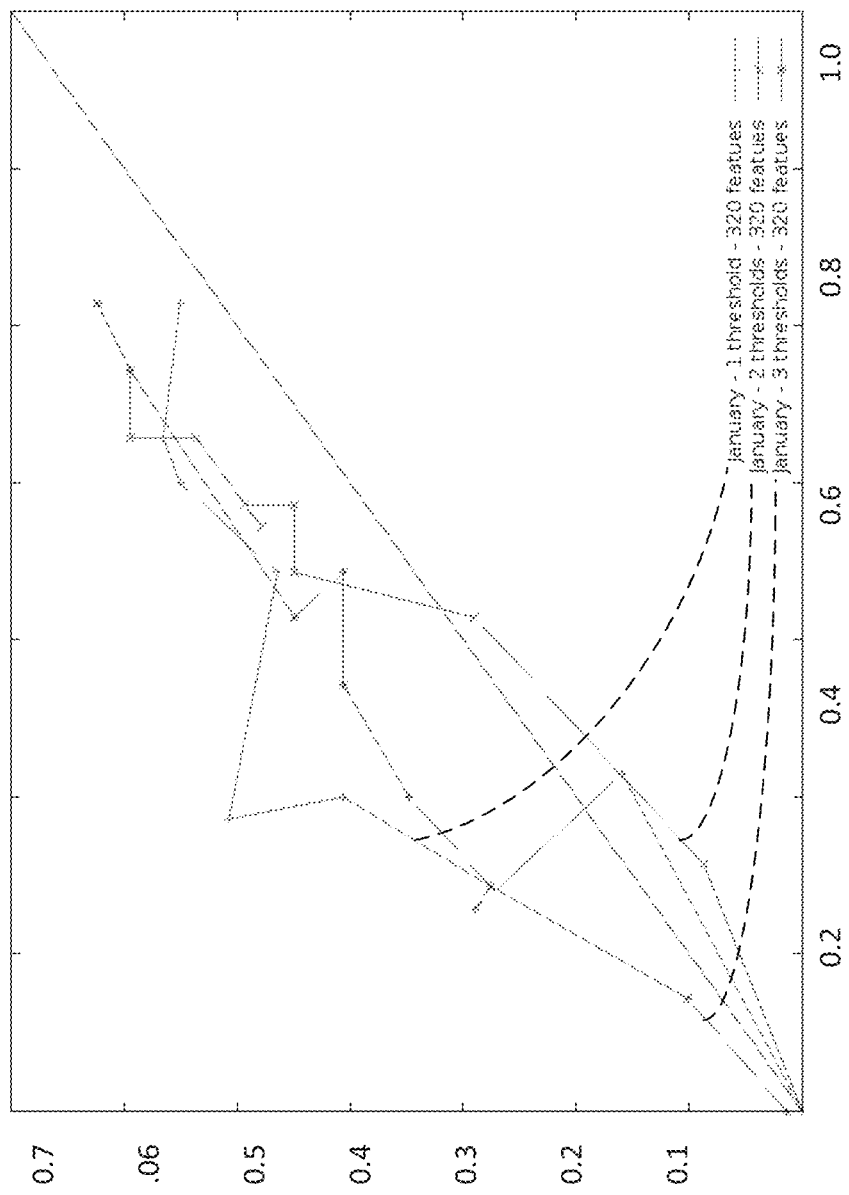

Referring to FIG. 4B, a graph plot of ROC Curve, Group 3 vs. Group 2 is shown. This graph shows the (ROC) obtained for three different sets of training parameters. Each data point is obtained via one run of 5-fold cross-validation, for a fixed set of parameters. Each collection of line segments is the result of training so as to maximize, while holding the nominal recall rate at or above a minimum required value. Every model obtained typically scores 97% to 100% in precision, on the training set (that is, on the training set, the ROC curve would live in the upper-left-hand corner). The red line along the diagonal indicates the expected score for models classifying purely by random chance. Three different training runs are shown. A run with 2 thresholds partitions the input word-counts into 3 features. The data shown is for the Clean dataset, including of 70 patients in group 3 and 69 in group 2.

Figure 4C:
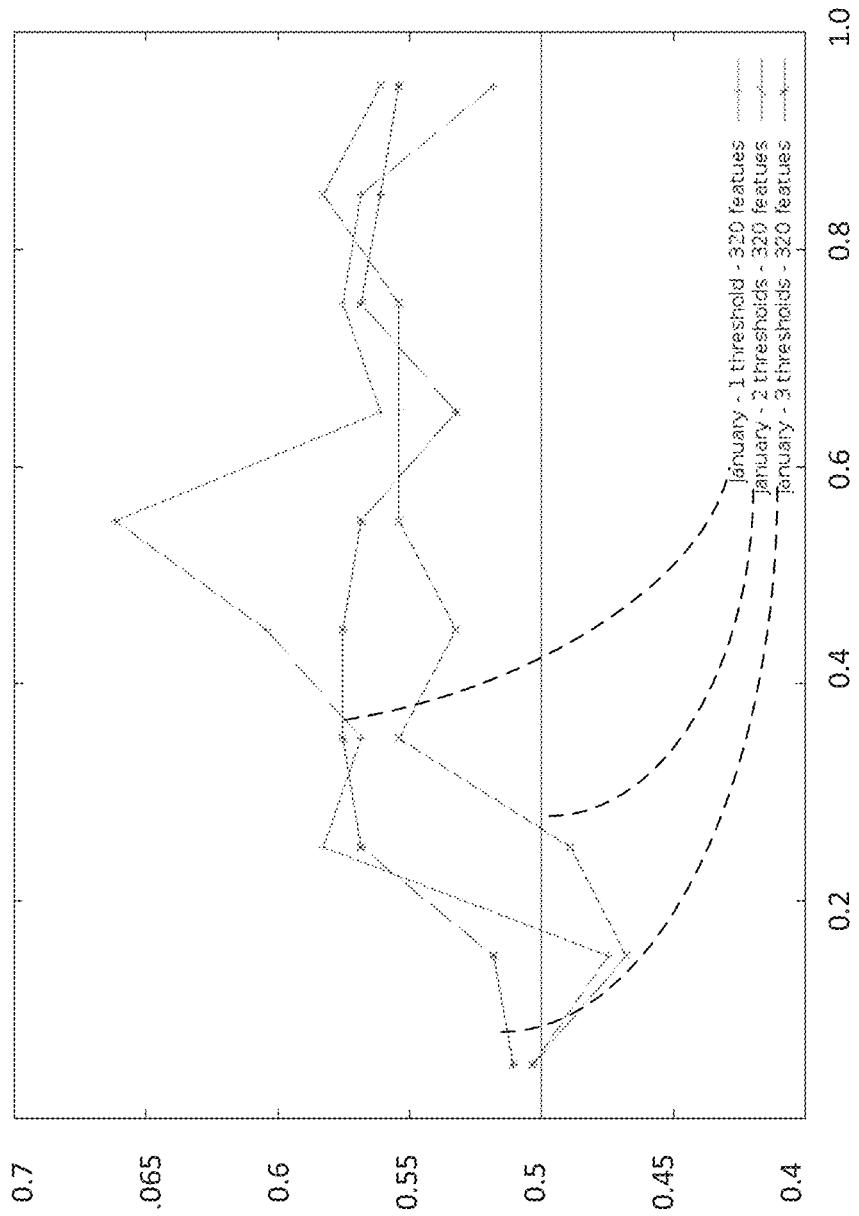

Referring to FIG. 4C, a graph plot of Accuracy, Group 3 vs. Group 2 is shown. This graph shows the accuracy on the test set, as a function of the nominal training-set recall. These curves are from the same data as graphed for the ROC in FIG. 4A. The models are trained so as to maximize precision, while holding the recall above a minimum level: the "nominal training recall" is that minimum level.

Model Derived Features (A∩B)

After models are trained and validated, those words that are high value features are extracted and word counts are produced for each. This allows for at least a frequency analysis on the part of an analyst to better understand key terms that visually differentiate the cohorts to accurately classify the three cohorts unsupervised.

"va1-model-word-freq.txt" derived from Cohort 1 vs. Cohort 2 model, with word counts from Cohort 1 only "va1-vs-2-model-word-freq.txt" derived from Cohort 1 vs. Cohort 2 model, with word counts from Cohort 2 only "va3-vs-2-model-word-freq.txt" derived from Cohort 3 vs. Cohort 2 model, with word counts from Cohort 2 only "va1-model-word-freq.txt" derived from Cohort 3 vs. Cohort 2 model, with word counts from Cohort 3 only Results of the words and counts can be shown visually in a 'Word Tag Cloud' format see Martin Halvey and Mark T. Keane, An Assessment of Tag Presentation Techniques, poster presentation at WWW 2007, 2007 http://www2007.org/htmlposters/poster988 incorporated herein by reference. Alternatively, the predictive terms can be listed or other approaches can be used.

Figure 5:
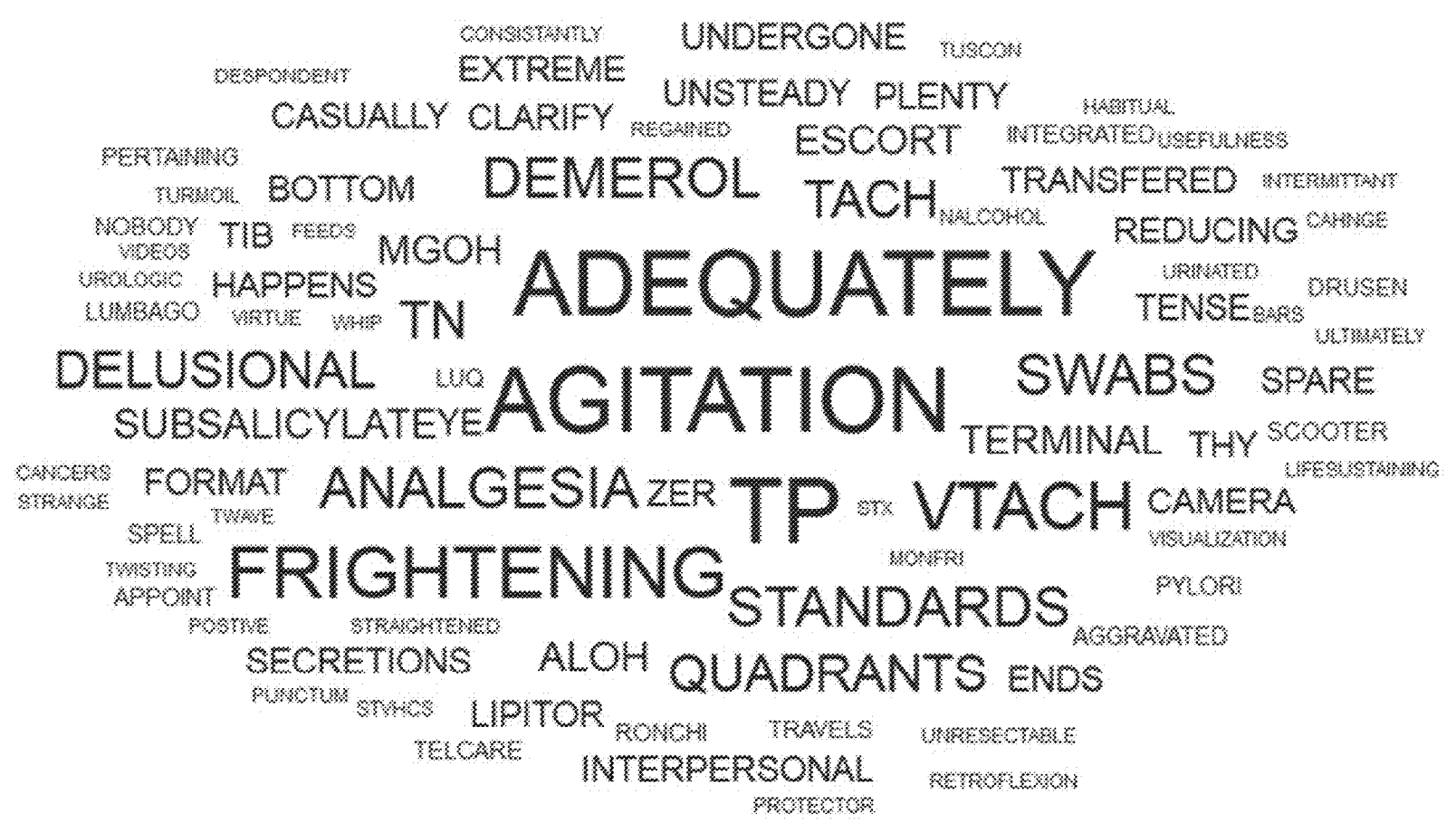

Referring now to FIG. 5 an exemplary word cloud presentation is show for the words Red group that contains the actual predictive terms for the suicide group 1. Word cloud presentations graphically depict the predictive terms and arrange the highly predictive terms in larger fonts in the display as shown. Word cloud presentations can be provided for all groups such as words from the Non-Psychiatric Control Group 1; Suicide Positive Group 2 vs. Control Group 1; words from the Suicide Positive Group 2 vs. Control Group 3; words from the Psychiatric Control Group 3, etc. The process can provide a difference (AΔB) by further subdividing the features into words that are only found in the corresponding cohorts. As such, these words can be shown in a word cloud presentation that is labeled Green (for Group 1) shown in FIG. 5, Yellow (for Group 3), and Red (for Group 2). These unique words can then be used for a simplified classification between cohorts.

Furthermore, by stepping through the analysis workflow of dataset statistical collection (A∪B) to model building (A|B) to deriving model features (A∩B) to feature difference (AΔB) provides a new process in statistical machine learning generally, and particularly one that can adapted for categorization of Psychological Cohorts. The process takes data sets of words associated with multiple groups within mental health (A∪B) and builds a classification model of one group vs. another (A|B). The process examines points of intersection (A∩B), and splits out words that are unique to each (AΔB) This resulting process, A∪B->A|B->A∩B->AΔB, produces a workflow that isolates the statistically predictive terms from multiple cohorts resulting in the exact pinpointing predictive features. Specifically, the prediction models can be suicidality predictive models.

Classifiers that distinguish mental state among three groups of patients are trained based on patient records. An accuracy of 0.58 is obtained for distinguishing group 1 and 2 patient records, and an accuracy of 0.65 is obtained for distinguishing group 2 and 3 patient records, for the Clean dataset.

The word counts for the words that distinguish the various groups can be revealing. In the Clean dataset, words such as "worthlessness" appear far more often in group 2 than in the other groups. The word "despondent" appears only in group 2, and there are highly elevated counts of the words "agitation" and "aid" in this group. By contrast, some words are noticeable by their absence: the words "crying" and "aggravating" are absent or nearly absent in group 2, and appear primarily in group 3. This may be due to a difference in the psychological coping abilities and strategies in these two groups, although it may also reflect the small sample size. In the same vein, "obesity" appears half as often in group 2 as in group 3. With a richer context, such as the inclusion of word phrases an approach used with corpus linguistics, such differences could be explained.

Specific words and counts can alternatively be listed as set out below in addition to or in lieu of word tag cloud representations.

Green_Results

| | | | |
|---|---|---|---|
| Rart: 17 | Nw: 9 | Modification: 5 | Polyphagia: 3 |
| Alphabetized: 17 | Dfe: 9 | Fatal: 5 | Optical: 3 |
| Plasma: 16 | Neutral: 8 | Dlco: 5 | Miw: 3 |
| Arthralgia: 14 | Poh: 7 | Sutured: 4 | Ladders: 3 |
| Perfusion: 13 | Blindness: 7 | Pls: 4 | Fluvirin: 3 |
| Vessel: 10 | Anorexia: 7 | Gram: 4 | Finger stick: 3 |
| myalgias: 10 | Ccs: 6 | Calculation: 4 | |
| Shampoo: 9 | Catheterization: 6 | Riding: 3 | |

Red_Results

| | | | |
|---|---|---|---|
| Agitation: 24 | Tense: 7 | Pylori: 5 | Protector: 2 |
| Adequately: 23 | Secretions: 7 | Lumbago: 5 | Positive: 2 |
| Analgesia: 15 | Clarify: 7 | Integrated: 5 | Life sustaining: 2 |
| Demerol: 13 | Camera: 7 | Aggravated: 5 | Tp: 24 |
| Tn: 11 | Bottom: 7 | Telcare: 4 | Frightening: 18 |
| Delusional: 11 | Reducing: 6 | Scooter: 4 | Vtach: 17 |
| Terminal: 9 | Plenty: 6 | Pertaining: 4 | Standards: 14 |
| Escort: 9 | Interpersonal: 6 | Habitual: 3 | Swabs: 13 |
| Unsteady: 8 | Extreme: 6 | Feeds: 3 | Tach: 12 |
| Transferred: 8 | Ends: 6 | Urologic: 2 | Quadrants: 11 |
| Happens: 8 | Casually: 6 | Twisting: 2 | Mgoh: 10 |
| Format: 8 | Ronchi: 5 | Retro flexion: 2 | Aloh: 10 |
| Subsalicylate: 9 | Nobody: 5 | Tuscon: 3 | Twave: 2 |
| Zero: 8 | Drusen: 5 | Stx: 3 | Turmoil: 2 |
| Ye: 7 | Appoint: 5 | Stvhcs: 3 | Regained: 2 |
| Tib: 7 | Luq: 4 | Strange: 3 | Alcohol: 2 |
| Thy: 7 | Whip: 3 | Straightened: 3 | Monfri: 2 |
| Lipitor: 7 | Visualization: 3 | Punctum: 3 | Intermittent: 2 |
| Undergone: 6 | Virtue: 3 | Consistently: 3 | Despondent: 2 |
| Spare: 6 | Urinated: 3 | Bars: 3 | Cancers: 2 |
| Travels: 5 | Unrespectable: 3 | Videos: 2 | Change: 2 |
| Spell: 5 | Ultimately: 3 | Usefulness: 2 | |

Yellow_Results

| | | | |
|---|---|---|---|
| Neut: 25 | Unmarried: 6 | Xpatient: 3 | Prefilled: 2 |
| Unique: 16 | Stain: 6 | Ues: 3 | Oween: 2 |
| Disheveled: 16 | Preoccupied: 6 | Teaspoonful: 3 | Mealtime: 2 |
| Presbyopia: 12 | Notably: 6 | Porter: 3 | Jef: 2 |
| Practicing: 10 | Epidermal: 6 | Well-groomed: 2 | Geropsychiatry: 2 |
| Bronze: 10 | Outstanding: 5 | Visa: 2 | Effected: 2 |
| Wounded: 8 | Anand: 5 | Tfts: 2 | Dpt: 2 |
| Blockers: 8 | Unpleasant: 4 | Supervisors: 2 | Directory: 2 |
| Warrant: 7 | Teacher: 4 | Subluxation: 2 | Arouse: 2 |
| Tempopormand: 7 | Su: 4 | Styles: 2 | Alignment: 2 |
| Ranges: 7 | Struggles: 4 | Splitting: 2 | |
| Demonstrating: 7 | Dent: 4 | Ruminates: 2 | |

Va1-Model-Word-Freq

| | | | |
|---|---|---|---|
| Screening: 147.0 | Educated: 25.0 | Aid: 14.0 | Techniques: 8.0 |
| Am: 142.0 | Stenosis: 23.0 | Wanted: 13.0 | Neutral: 8.0 |
| Activity: 132.0 | Private: 22.0 | Triglyceride: 13.0 | Land: 8.0 |
| Who: 87.0 | Category: 21.0 | Perfusion: 13.0 | Helping: 8.0 |
| Os: 78.0 | Postop: 20.0 | Admits: 13.0 | Experiencing: 8.0 |
| Years: 77.0 | Ready: 19.0 | Tetanus: 12.0 | Diagnostic: 8.0 |
| Triage: 74.0 | Yester: 18.0 | Centers: 12.0 | Accident: 8.0 |
| Neck: 68.0 | Requests: 18.0 | Already: 12.0 | Walkin: 7.0 |
| Requesting: 64.0 | Eggs: 18.0 | Recheck: 11.0 | Spinal: 7.0 |
| Adr: 62.0 | Verification: 17.0 | Purposes: 11.0 | Reasons: 7.0 |
| Appropriate: 49.0 | Tried: 17.0 | Images: 11.0 | Poh: 7.0 |
| While: 47.0 | Rart: 17.0 | Filled: 11.0 | Nothing: 7.0 |
| Again: 45.0 | Once: 17.0 | Ears: 11.0 | Lipids: 7.0 |
| Arthritis: 41.0 | Got: 17.0 | Vessel: 10.0 | Else: 7.0 |
| Exercise: 39.0 | Alphabetized: 17.0 | Received: 10.0 | Blindness: 7.0 |
| Read: 36.0 | Plasma: 16.0 | myalgia: 10.0 | Anorexia: 7.0 |
| Affect: 36.0 | Laboratory: 15.0 | African: 10.0 | Allow: 7.0 |
| Verbalized: 35.0 | Compensation: 15.0 | Shampoo: 9.0 | Accepted: 7.0 |
| Issue: 34.0 | Alteration: 15.0 | Screened: 9.0 | Verbally: 6.0 |
| Went: 33.0 | Takes: 14.0 | Nw: 9.0 | Thru: 6.0 |
| Returned: 30.0 | Memorial: 14.0 | Guillain-Barre: 9.0 | Tell: 6.0 |
| Uary: 27.0 | Hgbac: 14.0 | Die: 9.0 | Served: 6.0 |
| Try: 25.0 | Arthralgia: 14.0 | Bruit: 9.0 | Points: 6.0 |
| Moving: 6.0 | Startled: 5.0 | Calculation: 4.0 | City: 3.0 |
| Live: 6.0 | Sees: 5.0 | Brochure: 4.0 | Actually: 3.0 |
| Items: 6.0 | Modification: 5.0 | Alternatives: 4.0 | Ow: 2.0 |
| Half: 6.0 | Fatal: 5.0 | Absence: 4.0 | His: 2.0 |
| Foods: 6.0 | Dlco: 5.0 | Worried: 3.0 | Comp: 2.0 |
| Fatigue: 6.0 | Comprehensive: 5.0 | Specialist: 3.0 | Wife's: 1.0 |
| Documents: 6.0 | Wishes: 4.0 | Seeking: 3.0 | Whole: 1.0 |
| Declines: 6.0 | Sutured: 4.0 | Riding: 3.0 | Triggers: 1.0 |
| Ccs: 6.0 | Soon: 4.0 | Polyphagia: 3.0 | Syst: 1.0 |
| Catheterization: 6.0 | Revealed: 4.0 | Optical: 3.0 | Periodically: 1.0 |
| Addition: 6.0 | Responsibilities: 4.0 | Miw: 3.0 | Cutting: 1.0 |
| Accuracy: 6.0 | PIs: 4.0 | Ladders: 3.0 | Clothes: 1.0 |
| Wish: 5.0 | Intermittent: 4.0 | Fluvirin: 3.0 | |
| Wbc: 5.0 | Gram: 4.0 | Finger stick: 3.0 | |
| Trial: 5.0 | Cultural: 4.0 | Door: 3.0 | |

Va2-Vs-1-Model-Word-Freq

| | | | |
|---|---|---|---|
| Am: 402.0 | Appropriate: 136.0 | Read: 85.0 | Private: 52.0 |
| Who: 302.0 | Years: 135.0 | Went: 80.0 | Tried: 51.0 |
| Activity: 208.0 | Verbalized: 125.0 | Exercise: 76.0 | Accident: 51.0 |
| Screening: 207.0 | Yester: 117.0 | Returned: 71.0 | Wanted: 50.0 |
| Neck: 179.0 | Again: 105.0 | Issue: 67.0 | Takes: 49.0 |
| Triage: 158.0 | While: 104.0 | Got: 63.0 | Requests: 49.0 |
| Requesting: 146.0 | Aid: 93.0 | Educated: 54.0 | Ready: 45.0 |
| Affect: 137.0 | Once: 88.0 | Try: 52.0 | Laboratory: 45.0 |
| Already: 43.0 | Adequately: 23.0 | Specialist: 17.0 | Whole: 9.0 |
| Door: 42.0 | Sees: 22.0 | Points: 17.0 | Terminal: 9.0 |
| Tetanus: 41.0 | Nothing: 22.0 | Declines: 17.0 | Postop: 9.0 |
| Diagnostic: 39.0 | Alternatives: 22.0 | Clothes: 17.0 | Escort: 9.0 |
| Items: 33.0 | Allow: 22.0 | Syst: 16.0 | Cutting: 9.0 |
| Admits: 33.0 | Images: 21.0 | Screened: 16.0 | Unsteady: 8.0 |
| Comprehensive: 32.0 | Experiencing: 21.0 | Triggers: 15.0 | Transferred: 8.0 |
| Cultural: 31.0 | Documents: 21.0 | Ow: 15.0 | Happens: 8.0 |
| Live: 28.0 | Accepted: 20.0 | Helping: 15.0 | Format: 8.0 |
| Filled: 25.0 | Thru: 19.0 | Ears: 15.0 | Tense: 7.0 |
| Category: 25.0 | Served: 19.0 | Analgesia: 15.0 | Secretions: 7.0 |
| Verbally: 24.0 | Moving: 19.0 | Ad r: 15.0 | Periodically: 7.0 |
| Recheck: 24.0 | Alteration: 19.0 | Trial: 14.0 | Eggs: 7.0 |
| Intermittent: 24.0 | Wbc: 18.0 | Spinal: 14.0 | Clarify: 7.0 |
| Agitation: 24.0 | Revealed: 18.0 | Purposes: 14.0 | Camera: 7.0 |
| Wishes: 23.0 | Responsibilities: 18.0 | Foods: 14.0 | Bottom: 7.0 |
| Wish: 23.0 | received: 18.0 | Demerol: 13.0 | Reducing: 6.0 |
| Walking: 23.0 | Lipids: 18.0 | Actually: 13.0 | Plenty: 6.0 |
| Tell: 23.0 | Else: 18.0 | Absence: 13.0 | Interpersonal: 6.0 |
| Soon: 23.0 | City: 18.0 | Startled: 12.0 | Extreme: 6.0 |
| Reasons: 23.0 | Brochure: 18.0 | Seeking: 12.0 | Ends: 6.0 |
| His: 23.0 | Addition: 18.0 | Tn: 11.0 | Comp: 6.0 |
| Half: 23.0 | Worried: 17.0 | Os: 11.0 | Casually: 6.0 |
| | | Delusional: 11.0 | Arthritis: 6.0 |

-continued

| | | | |
|---|---|---|---|
| Fatigue: 23.0 | Techniques: 17.0 | Wife's: 10.0 | Verification: 5.0 |
| Uary: 5.0 | African: 5.0 | Feeds: 3.0 | Life sustaining: 2.0 |
| Stenosis: 5.0 | Triglyceride: 4.0 | Compensation: 3.0 | Centers: 2.0 |
| Ronchi: 5.0 | Tel-care: 4.0 | Urologic: 2.0 | Memorial: 1.0 |
| Pylori: 5.0 | Scooter: 4.0 | Twisting: 2.0 | Land: 1.0 |
| Lumbago: 5.0 | Pertaining: 4.0 | Retro flexion: 2.0 | Hgbac: 1.0 |
| Integrated: 5.0 | Habitual: 3.0 | Protector: 2.0 | Bruit: 1.0 |
| Aggravated: 5.0 | Guillain-Barre: 3.0 | Positive: 2.0 | Accuracy: 1.0 |

Va2-Vs-3-Model-Word-Freq

| | | | |
|---|---|---|---|
| Vet: 716.0 | Teeth: 33.0 | Te: 17.0 | Aaa: 8.0 |
| About: 629.0 | Ucinations: 31.0 | Upcoming: 16.0 | Ye: 7.0 |
| When: 475.0 | Docusate: 25.0 | Street: 16.0 | Warning: 7.0 |
| Visit: 441.0 | Aa: 25.0 | Standards: 14.0 | Uncooperative: 7.0 |
| Year: 287.0 | Tp: 24.0 | Shave: 14.0 | Uc: 7.0 |
| Disorder: 254.0 | Walkin: 23.0 | Swabs: 13.0 | Top: 7.0 |
| Symptoms: 226.0 | Temazepam: 22.0 | Tach: 12.0 | Tib: 7.0 |
| lcdcm: 177.0 | Student: 22.0 | Quadrants: 11.0 | Thy: 7.0 |
| Telemetry: 102.0 | Restricted: 22.0 | Fear: 11.0 | Lipitor: 7.0 |
| Ssn: 100.0 | Willing: 21.0 | Reorder: 10.0 | Alot: 7.0 |
| Verified: 83.0 | Supply: 21.0 | Mgoh: 10.0 | Watches: 6.0 |
| Private: 52.0 | Adult: 20.0 | Aloh: 10.0 | Unt: 6.0 |
| Voiding: 49.0 | Trazodone: 19.0 | Worthlessness: 9.0 | Undergone: 6.0 |
| Specimen: 41.0 | Frightening: 18.0 | Subsalicylate: 9.0 | Transfusions: 6.0 |
| He: 39.0 | Vtach: 17.0 | Zer: 8.0 | Topical: 6.0 |
| Obesity: 35.0 | Unchanged: 17.0 | Valley: 8.0 | Spare: 6.0 |
| Younger: 5.0 | Whip: 3.0 | nocturnal: 3.0 | Monfri: 2.0 |
| Wtih: 5.0 | Visualization: 3.0 | consistently: 3.0 | Intermittent: 2.0 |
| Volume: 5.0 | Virtue: 3.0 | Bars: 3.0 | Despondent: 2.0 |
| Vit: 5.0 | Urinated: 3.0 | Ant: 3.0 | Crying: 2.0 |
| Travels: 5.0 | Unrespectable: 3.0 | Aggravating: 3.0 | Cancers: 2.0 |
| Spell: 5.0 | Ultimately: 3.0 | Videos: 2.0 | Change: 2.0 |
| Nobody: 5.0 | Tuscon: 3.0 | Usefulness: 2.0 | Unsp: 1.0 |
| Drusen: 5.0 | Supervisor: 3.0 | Twave: 2.0 | Unhappy: 1.0 |
| Appoint: 5.0 | Stx: 3.0 | Turmoil: 2.0 | Ton: 1.0 |
| Antipsychotic: 5.0 | Stvhcs: 3.0 | Thi: 2.0 | Psychiatrically: 1.0 |
| Style: 4.0 | Strange: 3.0 | Residential: 2.0 | |
| Luq: 4.0 | Straightened: 3.0 | Regained: 2.0 | |
| Afraid: 4.0 | Punctum: 3.0 | Nalcohol: 2.0 | |

Va3-Model-Word-Freq

| | | | |
|---|---|---|---|
| Visit: 847.0 | Teeth: 97.0 | Shave: 42.0 | Unt: 29.0 |
| About: 761.0 | Specimen: 78.0 | Willing: 40.0 | Unchanged: 28.0 |
| Vet: 739.0 | Obesity: 73.0 | Top: 39.0 | Voiding: 26.0 |
| When: 594.0 | Volume: 70.0 | Trazodone: 38.0 | Neut: 25.0 |
| Disorder: 392.0 | Student: 62.0 | Hc: 38.0 | Fear: 23.0 |
| Year: 343.0 | Ucinations: 61.0 | Upcoming: 37.0 | Topical: 20.0 |
| Symptoms: 311.0 | Walkin: 54.0 | Adult: 35.0 | Warning: 19.0 |
| lcdcm: 308.0 | Aa: 49.0 | Supervisor: 34.0 | Private: 19.0 |
| Ssn: 121.0 | Supply: 47.0 | Unsp: 31.0 | Aggravating: 19.0 |
| Verified: 105.0 | Street: 46.0 | Docusate: 30.0 | Vit: 18.0 |
| Unique: 16.0 | Unhappy: 6.0 | Supervisors: 2.0 | |
| Nocturia: 16.0 | Thi: 6.0 | Subluxation: 2.0 | |
| Disheveled: 16.0 | Stain: 6.0 | Styles: 2.0 | |
| Alot: 16.0 | Preoccupied: 6.0 | Splitting: 2.0 | |
| Style: 14.0 | Notably: 6.0 | Ruminates: 2.0 | |
| Restricted: 13.0 | Epidermal: 6.0 | Reorder: 2.0 | |
| Residential: 13.0 | Outstanding: 5.0 | Prefilled: 2.0 | |
| Crying: 13.0 | Anand: 5.0 | Oween: 2.0 | |
| Afraid: 13.0 | Unpleasant: 4.0 | Mealtime: 2.0 | |
| Presbyopia: 12.0 | Uc: 4.0 | Jef: 2.0 | |
| Ton: 11.0 | Teacher: 4.0 | Neuropsychiatry: 2.0 | |
| Practicing: 10.0 | Te: 4.0 | | |
| Bronze: 10.0 | Su: 4.0 | Effected: 2.0 | |
| Ant: 9.0 | Struggles: 4.0 | Dpt: 2.0 | |
| Wounded: 8.0 | Dent: 4.0 | Directory: 2.0 | |
| Telemetry: 8.0 | Xpatient: 3.0 | Arouse: 2.0 | |
| Psychiatrically: 8.0 | Ues: 3.0 | Antipsychotic: 2.0 | |
| Blockers: 8.0 | Teaspoonful: 3.0 | Alignment: 2.0 | |

-continued

| | | |
|---|---|---|
| Warrant: 7.0 | Porter: 3.0 | Younger: 1.0 |
| Tempopormand: 7.0 | Worthlessness: 2.0 | Wtih: 1.0 |
| Temazepam: 7.0 | Well-groomed: 2.0 | Valley: 1.0 |
| Ranges: 7.0 | Watches: 2.0 | Transfusions: 1.0 |
| Demonstrating: 7.0 | Visa: 2.0 | Aaa: 1.0 |
| Unmarried: 6.0 | Uncooperative: 2.0 | |
| | Tfts: 2.0 | |

Embodiments can be implemented in digital electronic circuitry, or in computer hardware, firmware, software, or in combinations thereof. Apparatus of the invention can be implemented in a computer program product tangibly embodied or stored in a machine-readable storage device for execution by a programmable processor; and method actions can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD_ROM disks. Any of the foregoing can be supplemented by, or incorporated in, ASICs (application-specific integrated circuits).

Other embodiments are within the scope and spirit of the description claims. For example, due to the nature of software, functions described above can be implemented using software, hardware, firmware, hardwiring, or combinations of any of these. Features implementing functions may also be physically located at various positions, including being distributed such that portions of functions are implemented at different physical locations.

What is claimed is:

1. A computer implemented process comprises:
producing by one or more computers plural sets of training data that comprise words associated with multiple groups of individuals, with the multiple groups being of individuals having different classifications of mental states that define a like number of multiple cohorts;
executing by one or more computers a classification model using the training data to classify a first group of individuals in relation to a second, different group of individuals, with the first and second groups of individuals being of the multiple groups of individuals, and different ones of the multiple cohorts;
determining by one or more computers points of intersection of words between the first group and the second group of individuals;
determining by one or more computers words in the training data that are unique to the first group of individuals to provide isolated statistically predictive terms for the first group to identify predictive features for a first cohort; and
determining by one or more computers words in the training data that are unique to the second group of individuals to provide isolated statistically predictive terms for the second group to identify predictive features for a second one of the cohorts.

2. The method of claim 1 further comprising:
determining by the one or more computers a prediction of mental health status of the groups.

3. The method of claim 2 wherein the prediction is of suicidality risk.

4. The method of claim 2 wherein the prediction is suicidal ideation.

5. The method of claim 1 further comprising applying by the one or more computers a military veteran population dataset for suicidality prediction.

6. The method of claim 1 further comprising;
forming by the one or more computers 'contextualized word pairs' to improve predictive accuracy.

7. The method of claim 1 wherein determining the model comprises
applying a machine learning system, including Bayesian algorithms to the dataset to predict mental state.

8. The method of claim 1 further comprises
applying a machine learning system that includes genetic algorithms and genetic programming systems to predict mental state.

9. A computer implemented process comprises:
producing by one or more computers plural sets of training data that comprise words associated with multiple groups of individuals, with the multiple groups being of individuals having different mental states that define multiple cohorts;
executing by one or more computers a classification model using the training data to classify a first group of individuals in relation to a second, different group of individuals, with the first and second groups of individuals being of the multiple groups of individuals;
determining by one or more computers points of intersection of words between the first group and the second group of individuals;
determining by one or more computers words in the training data that are unique the first group of individuals and the second group of individuals to provide isolated statistically predictive terms for the first and second groups to identify predictive features for corresponding first and second cohorts; and
applying a workflow process to reduce complexity in classification of the first and second groups:

producing by the one or more computers a visualization of mental state cohorts for classification of risk.

10. The method of claim 9 further comprising:
determining by the one or more computers a prediction of mental health status of the groups.

11. A computer program product tangibly stored on a computer readable hardware storage device, the computer program product for mental state classification comprises instructions for causing a processor to:
produce plural sets of training data that comprise words associated with multiple groups of individuals, with the multiple groups of individuals having different classifications of mental states that define a like number of multiple cohorts;
execute a classification model on each of the sets of training data to classify a first group of individuals in relation to a second, different group of individuals, with the first and second groups of individuals being of the multiple groups of individuals, and different ones of the multiple cohorts;
determine points of intersection of words between the first group and the second group of individuals;
determine words in the training data that are unique to the first group of individuals to provide isolated statistically predictive terms for the first group to identify predictive features for a first cohort; and
determine words in the representations of the training data that are unique to the second group of individuals to provide isolated statistically predictive terms for the second group to identify predictive features for a second one of the cohorts.

12. The product of claim 11 further comprising instructions to:
determining by the one or more computers a prediction of mental health status of the groups.

13. The product of claim 11 wherein the prediction is of suicidality risk.

14. The product of claim 11 wherein the prediction is suicidal ideation.

15. The product of claim 11 further comprising applying by the one or more computers a military veteran population dataset for suicidality prediction.

16. The product of claim 11 further comprising instructions to:
form contextualized word pairs to improve predictive accuracy.

17. The product of claim 1 wherein determining the model comprises
apply a machine learning system, including Bayesian algorithms to the dataset to predict mental state.

18. The product of claim 11 further comprising instructions to
apply a machine learning system that includes genetic algorithms and genetic programming systems to predict mental state.

19. Apparatus, comprising:
a processor;
a memory coupled to the processor; and
a computer readable storage device storing a computer program product for mental state classification, the computer program product comprises instructions for causing the processor to:
produce plural sets of training data that comprise words associated with multiple groups of individuals, with the multiple groups of individuals having different classifications of mental states that define a like number of multiple cohorts;
execute a classification model on each of the sets to classify a first group of individuals in relation to a second, different group of individuals, with the first and second groups of individuals being of the multiple groups of individuals, and different ones of the multiple cohorts;
determine points of intersection of words between the first group and the second group of individuals;
determine words in the sets of the training data that are unique to the first group of individuals to provide isolated statistically predictive terms for the first group to identify predictive features for a first cohort; and
determine words in the sets of the training data that are unique to the second group of individuals to provide isolated statistically predictive terms for the second group to identify predictive features for a second one of the cohorts.

20. The apparatus of claim 19 wherein the product further comprising instructions to
apply a machine learning system that includes genetic algorithms and genetic programming systems to predict mental state.

* * * * *

UNITED STATES PATENT AND TRADEMARK OFFICE
CERTIFICATE OF CORRECTION

| | |
|---|---|
| PATENT NO. | : 9,817,949 B2 |
| APPLICATION NO. | : 13/803120 |
| DATED | : November 14, 2017 |
| INVENTOR(S) | : Christian D. Poulin et al. |

It is certified that error appears in the above-identified patent and that said Letters Patent is hereby corrected as shown below:

In the Specification

Column 1, Line 18, please insert the following:
--This U.S. patent is subject to a United States Government confirmatory license pursuant to a sub-contract under Contract No. N66001-11-C-4006, Modification P00001 between the Space and Naval Warfare Systems Command (SPAWAR Systems Center Pacific), part of the United States Department of the Defense (Navy).--

Signed and Sealed this
Thirteenth Day of December, 2022

Katherine Kelly Vidal
*Director of the United States Patent and Trademark Office*